US008981124B2

(12) United States Patent
Wautier et al.

(10) Patent No.: US 8,981,124 B2
(45) Date of Patent: Mar. 17, 2015

(54) PROCESS FOR THE MANUFACTURE OF A CYCLIC DIESTER OF AN ALPHA-HYDROXYACID

(75) Inventors: Henri Georges Ghislain Wautier, Braine le Comte (BE); Dominique Francois Achille Marchand, Saive (BE)

(73) Assignee: Solvay SA, Brussels (BE)

( * ) Notice: Subject to any disclaimer, the term of this patent is extended or adjusted under 35 U.S.C. 154(b) by 55 days.

(21) Appl. No.: 13/809,418

(22) PCT Filed: Jul. 8, 2011

(86) PCT No.: PCT/EP2011/061603
§ 371 (c)(1),
(2), (4) Date: Jan. 10, 2013

(87) PCT Pub. No.: WO2012/007379
PCT Pub. Date: Jan. 19, 2012

(65) Prior Publication Data
US 2013/0116448 A1    May 9, 2013

(30) Foreign Application Priority Data
Jul. 14, 2010 (EP) .................................. 10169481

(51) Int. Cl.
*C07D 319/12* (2006.01)

(52) U.S. Cl.
CPC .................................. *C07D 319/12* (2013.01)
USPC ........................................................... 549/274

(58) Field of Classification Search
USPC ........................................................... 549/274
See application file for complete search history.

(56) References Cited

U.S. PATENT DOCUMENTS

| 1,095,205 | A | 5/1914 | Gruter et al. |
| 2,668,162 | A | 2/1954 | Lowe |
| 3,322,791 | A | 5/1967 | Selman |
| 5,043,458 | A | 8/1991 | Bhatia |
| 5,374,743 | A | 12/1994 | Thayer et al. |
| 2009/0318713 | A1 | 12/2009 | Wajc |
| 2010/0010276 | A1 | 1/2010 | Vogel et al. |

FOREIGN PATENT DOCUMENTS

| DE | 102006055427 A1 | 5/2008 |
| WO | WO 9200292 A1 | 1/1992 |
| WO | WO 9319058 A2 | 9/1993 |
| WO | WO 9509142 A1 | 4/1995 |

*Primary Examiner* — Kristin Vajda

(57) ABSTRACT

Process for the manufacture of a cyclic diester of an alpha-hydroxyacid comprising heating the alpha-hydroxyacid at a temperature from 100 to 250° C. in the presence of at least one polyol and of at least one catalyst selected from the group consisting carboxylates and alkoxides of Ti, Zr, Al and Sn.

20 Claims, No Drawings

PROCESS FOR THE MANUFACTURE OF A CYCLIC DIESTER OF AN ALPHA-HYDROXYACID

CROSS-REFERENCE TO RELATED APPLICATIONS

This application is a U.S. national stage entry under 35 U.S.C. 371 of International Application No. PCT/EP2011/061603 filed Jul. 8, 2011, which claims priority to European application No. 10169481.8 filed on Jul. 14, 2010, the whole content of this application being incorporated herein by reference for all purposes.

The present invention relates to a process for the manufacture of a cyclic diester of an alpha-hydroxyacid. In particular, it relates to the manufacture of lactide or glycolide, the cyclic diesters of respectively lactic acid and glycolic acid.

Lactide and glycolide are key intermediates for the manufacture of polylactic acid (or polylactide) (PLA) and polyglycolic acid (or polyglycolide) (PGA), which are biodegradable, thermoplastic polymers derived from renewable resources. The synthesis of the lactide and of the glycolide is the most important step in the conventional PLA and PGA manufacturing processes. It is this step that will govern the price of the final polymer. The lactide and the glycolide must also be as pure as possible in order to be able to carry out the ring-opening polymerization leading to corresponding PLA and PGA with high molecular weights.

The preparation of cyclic diesters of alpha-hydroxyacids is usually conducted in two distinct steps involving first preparing an oligomer of the alpha-hydroxyacid, i.e. a relatively short chain condensation polymer thereof having typically a molecular weight of a few thousands g/mol, then heating the oligomer under reduced pressure to generate the desired cyclic diester. Such a process is for instance disclosed in U.S. Pat. No. 1,095,205 for lactide synthesis, in U.S. Pat. No. 2,668,162 for glycolide synthesis, or in U.S. Pat. No. 5,374,743 for both lactide and glycolide synthesis.

This process has the disadvantage to require a lot of energy and to lead to impure products requiring further purification steps and the treatment of the by-products. A further drawback is linked to the yield of this classical process which is usually of about 50%, due to the degradation of the oligomers at high temperature.

Direct syntheses of lactide or glycolide have also been disclosed. For example, U.S. Pat. No. 3,322,791 discloses the preparation of lactide by heating lactic acid at a temperature of 100 to 250° C. in the presence of 0.01 to 5 wt %, based on the weight of lactic acid, of a titanium alkoxide containing up to 12 carbon atoms in the alkoxide radical. This process seems to be advantageous in view of the classical polymerization/depolymerization process but the yield is still quite limited, being of only 60%. Attempts have also been made to synthesize cyclic diesters of alpha-hydroxyacids in vapor phase, as disclosed in international patent application WO92/00292 or WO93/19058. Such vapor phase processes require specific equipment and a lot of energy. The degradation as well as the polymerization of the alpha-hydroxyacid must also be avoided during its vaporization. Another example is given by international patent application WO93/19058 which discloses the direct synthesis of cyclic diesters of hydroxyacids, in particular lactide, by removing water from a feedstream comprising the hydroxyacid until a polymerization degree of less than or equal to 4 is attained. This process leads to the production of many by-products, requires important additional separation and purification steps and leads to a very low yield, well below 50%. International patent application WO93/19058 also discloses the possibility to produce cyclic diesters of hydroxyacids by azeotropic distillation of a diluted solution of the alpha-hydroxyacid in an organic solvent. Such a method has the main drawback to require the use of a huge amount of organic solvents, especially aromatic solvents such as benzene or toluene, or of solvents such as acetonitrile, which is not compatible with an environmental friendly process. This is especially not compatible with the synthesis of "green" polymers such as PLA and PGA, manufactured from bio-sourced lactide or glycolide. Recently, US 2009/0318713 has disclosed a process for the synthesis of lactide by reacting the calcium or magnesium salt of the lactic acid with a strong acid, the salt of which with the metal being hygroscopic, to obtain the cyclic diester dispersed in the hygroscopic salt. This process requires first the preparation of the lactic acid metal salt. Then, by reacting said lactic acid metal salt with a strong acid, it leads to a huge amount of salts, such as calcium sulfate, that needs to be treated or destroyed, which is not environmentally friendly. Another disadvantage of this process is its low yield, below 50%.

The purpose of the present invention is to provide a process for the synthesis of cyclic diesters of alpha-hydroxyacids, particularly for the synthesis of lactide and glycolide, which does not present the above disadvantages. In particular, the purpose of the present invention is to provide an environmentally friendly, simple and economic process which enables the manufacture of the cyclic diesters with a high yield, without numerous subsequent separation and purification steps.

The present invention therefore relates to a process for the manufacture of a cyclic diester of an alpha-hydroxyacid comprising heating the alpha-hydroxyacid at a temperature from 100 to 250° C. in the presence of at least one polyol and of at least one catalyst selected from the group consisting carboxylates and alkoxides of Ti, Zr, Al and Sn.

Indeed, it has been surprisingly found that, when heated in the presence of a polyol and of a catalyst according to the present invention, the alpha-hydroxyacid readily forms the corresponding cyclic diester which can be easily separated from the reaction medium, for example by distillation.

In the process of the present invention, the alpha-hydroxyacid may be any kind of alpha-hydroxyacid, in particular lactic acid, glycolic acid, glucaric acid, mandelic acid, malic acid, citric acid and tartaric acid; preferably lactic acid and glycolic acid; in particular glycolic acid. It has to be noted that all these alpha-hydroxyacids can form cyclic diesters. Nevertheless, some differences exist between the reactivity of these various acids. For instance, when comparing glycolic acid and lactic acid, it can be seen that glycolic acid comprises a primary alcohol while lactic acid comprises a secondary alcohol. This difference implies a higher reactivity of the glycolic acid, which could lead to undue oligomerization of the acid or undue hydrolization of the glycolide compared to the lactide.

One of the essential features of the present invention resides in the use of the polyol. It has indeed been found that, in the absence of the polyol, lower yields are obtained, or even no cyclic diester is produced at all. The polyol may be selected from the group consisting of ethylene glycol (or monoethylene glycol or glycol), propylene glycol, diethylene glycol, glycerol, erythritol, mannitol, sorbitol, xylitol, maltitol, lactitol, and volemitol, preferably from ethylene glycol, propylene glycol, diethylene glycol, and glycerol, in particular from ethylene glycol. The polyol is typically added in an amount of from 2 to 50 mol % of the alpha-hydroxyacid, especially from 5 to 20 mol %, for instance about 10 mol %. Depending on its molecular weight, the polyol amount is usually from 1 to 40 wt % of the alpha-hydroxyacid, particularly from 2 to 20 wt %, more particularly from 3 to 15 wt %, for example about 5 to 10 wt %.

Another essential feature of the present invention is the choice of the catalyst which is selected from the group consisting carboxylates (RCOO⁻) and alkoxides (RO⁻) of titanium (Ti), zirconium (Zr), aluminum (Al) and tin (Sn), especially from titanium carboxylates, titanium alkoxides, tin carboxylates, and tin alkoxides, particularly from titanium alkoxides. Carboxylates are for example acetates (OAc), octanoates or ethyl-2-hexanoates. Alkoxides are for example methoxides (OMe), ethoxides (OEt), propoxides (OM, isopropoxides (OiPr), n-butoxides (OBu), or isobutoxides (OiBu). For instance, the catalyst may be selected from titanium tetraacetate (Ti(OAc)$_4$), titanium tetramethoxide, (Ti(OMe)$_4$), titanium tetraethoxide (Ti(OEt)$_4$), titanium tetraisopropoxide (Ti(OiPr)$_4$) or tin tetrabutoxide (Sn(OBu)$_4$), Ti(OEt)$_4$. In the process of the invention, the catalyst is usually added in an amount of from 5 to 5000 mppm (mol/mol) of the alpha-hydroxyacid, more often from 10 to 500 mppm, most often from 50 to 300 mppm. The catalyst amount is often from 15 to 15000 wppm (wt/wt) of the alpha-hydroxyacid, more often from 30 to 1500 wppm, most often from 100 to 1000 wppm. The catalyst is advantageously added as a solution in the polyol or as a solution in an optional solvent as defined below. Without being bound by any theory, it is believed that adding the catalyst as a solution rather than as a pure product avoids precipitation of the catalyst further to the hydrolysis of the Ti—OR bond.

In the present process, the alpha-hydroxyacid is typically heated in the presence of the polyol and of the catalyst at a temperature from 100 to 250° C., preferably from 150 to 240° C., more preferably from 180 to 230° C. Said heating may be conducted at atmospheric pressure are under reduced pressure, advantageously under reduced pressure, in particular under a pressure equal to or lower than 500 mbar, more particularly equal to or lower than 200 mbar, especially equal to or lower than 100 mbar. The pressure is generally equal to or higher than 1 mbar, especially equal to or higher than 5 mbar, more particularly equal to or higher than 10 mbar. In a preferred embodiment, the heating is initiated at atmospheric pressure then continues under a progressive vacuum until the required pressure is attained, especially until a pressure from 10 to 100 mbar, for instance about 10, 20, 30, 40 or 50 mbar. The heating time depends upon the reaction temperature and this parameter may be within wide ranges. Most often, the heating is conducted during 1 to 24 hours, preferably from 2 to 12 hours, more preferably from 4 to 8 hours, for instance around 6 hours. The reaction is effected preferably in the liquid phase. Advantageously, the water formed is removed from the reaction mixture, for instance by distillation.

The heating of the alpha-hydroxyacid in the presence of the polyol and of the catalyst may be conducted in the presence or in the absence of a solvent. If a solvent is present, it is usually added in an amount of from 5 to 100 wt % of the reaction medium, especially of from 10 to 50 wt %. If at least one solvent is added to the medium comprising the alpha-hydroxyacid, the polyol and the catalyst, it may be selected from any kind of suitable organic solvent, in particular from polar organic solvents, more particularly from protic polar organic solvents, especially from alcohols. In a preferred embodiment, the solvent has a sufficiently high boiling point, especially a boiling point of at least 80° C., with particular preference a boiling point of at least 100° C., with a higher preference a boiling point of at least 120° C. In an especially preferred embodiment, the solvent is more acidic than water, i.e. the solvent has an acid dissociation constant (pKa) lower than the pKa of water (15,7). Especially suitable solvents are selected from the group consisting of glycol ethers. Examples of glycol ethers are derivatives of ethylene glycol (R—O—(CH$_2$—CH$_2$)$_n$—O—R') or of propylene glycol (R—O—[CH$_2$—CH(CH$_2$)]$_n$—O—R), such as ethylene glycol monomethyl ether (or 2-methoxyethanol or methyl cellosolve), ethylene glycol monoethyl ether (or 2-ethoxyethanol), ethylene glycol monopropyl ether (or 2-propoxyethanol), ethylene glycol monoisopropyl ether (or 2-isopropoxyethanol), ethylene glycol monobutyl ether (or 2-butoxyethanol), ethylene glycol monophenyl ether (or 2-phenoxyethanol), ethylene glycol monobenzyl ether (or 2-benzyloxyethanol), diethylene glycol monomethyl ether (or 2-(2-methoxyethoxy)ethanol or methyl carbitol), diethylene glycol monoethyl ether (or 2-(2-ethoxyethoxy)ethanol or carbitol cellosolve), diethylene glycol mono-n-butyl ether (or 2-(2-butoxyethoxy)ethanol), ethylene glycol dimethyl ether (or dimethoxyethane), ethylene glycol diethyl ether (or diethoxyethane), ethylene glycol dibutyl ether (or dibutoxyethane), propylene glycol monomethyl ether (or 1-methoxy-2-propanol), propylene glycol monoethyl ether (or 1-ethoxy-2-propanol), propylene glycol monopropyl ether (or 1-propoxy-2-propanol), propylene glycol monobutyl ether, propylene glycol monophenyl ether, dipropylene glycol monomethyl ether.

The reaction may be conducted in any kind of reactor, for example in an agitated reactor. In an advantageous embodiment, the reaction can be conducted in a still or in a distillation apparatus which allows the removal of the water from the reaction mixture and which allows subsequent separation of the cyclic ester of the alpha-hydroxyacid from the reaction medium. Distillation systems suitable for this purpose are common knowledge and are frequently used for separation.

In a preferred embodiment, the alpha-hydroxyacid may be first heated prior to the addition of the polyol and of the catalyst, typically at a temperature from 80 to 150° C., preferably from 90 to 120° C. Said first heating may for instance be conducted during 1 to 48 hours, in particular from 12 to 36 hours. Said first heating is advantageously conducted at atmospheric pressure. Advantageously, water possibly formed during said heating step is removed from the medium by distillation, during or after the heating step. It is also possible to add water to the alpha-hydroxyacid prior to said first heating, to solubilize the alpha-hydroxyacid. Said water may be added in an amount of from 10 to 100% by weight of the alpha-hydroxyacid, in particular from 30 to 60%, for instance about 40 or 50%. Preferably, once the alpha-hydroxyacid is solubilized, the water, which includes the added water as well as water possibly formed during the heating step, is removed from the medium by distillation during or after the heating step.

After the heating of the alpha-hydroxyacid in the presence of the polyol and of the catalyst, the cyclic diester of the alpha-hydroxyacid may be collected, for instance by distillation, especially by distillation under reduced pressure, for instance by heating the reaction medium at a temperature from 160 to 260° C., for example from 215 to 240° C., under reduced pressure, for example at a pressure below 10 mbar, in particular equal to or lower than 5 mbar, especially equal to or lower than 3 mbar, more preferably equal to or lower than 1 mbar. The cyclic diester of the alpha-hydroxyacid may also be removed from the reaction mixture by extraction, for instance using toluene, acetone, tetrahydrofurane or methylene dichloride as an extraction solvent. This would be followed by evaporation of the extraction solvent or by crystallization from solution and separation.

The present invention thus also relates to a process for the manufacture of a cyclic diester of an alpha-hydroxyacid comprising the steps of:
(a) heating the alpha-hydroxyacid at a temperature from 80 to 150° C., during from 1 to 48 hours at atmospheric pressure,
(b) adding at least one polyol and at least one catalyst selected from the group consisting carboxylates and alkoxides of Ti, Zr, Al and Sn,
(c) heating the mixture at a temperature from 100 to 250° C., the heating being preferably conducted under reduced pressure, advantageously the heating being initiated at atmospheric pressure then continued under a progressive vacuum until a pressure of maximum 200 mbar is attained,
(d) recovering the cyclic diester of the alpha-hydroxyacid by distillation.

The cyclic diester of the alpha-hydroxyacid recovered can be used immediately for some applications, without further purification steps. The cyclic diester of the alpha-hydroxyacid may also be purified, for instance by distillation or chromatographic processes.

The present invention is further illustrated below without limiting the scope thereto.

Should the disclosure of any patents, patent applications, and publications which are incorporated herein by reference conflict with the description of the present application to the extent that it might render a term unclear, the present description shall take precedence.

EXAMPLES

In the following examples, a BÜCHI Glass Oven B-585 was used, equipped with a boiler (80 ml round-bottomed flask, called B1) and with a separate vessel in line with the boiler (called B2). In examples 1 to 6, vessel B1 was fully located in the oven and vessel B2 was located such that ⅓ was in the oven and ⅔ were out of the oven. In examples 7-11, vessel B1 was fully located in the oven and vessel was is located out of the oven.

Example 1

17.0 g of pure (99%) solid glycolic acid and 7.6 g of water (to solubilize the glycolic acid) were introduced into the 80 ml BÜCHI round-bottomed flask (B1) and said flask was placed in a ventilated oven at 110° C. during about 80 hours. After 80 hours, a white solid was present in B1 and 11.1 g of water were collected in B2.

1.41 g of distilled ethylene glycol (22.6 mmol or 45 mmol of OH functions) and 13 mg of a 34 wt % solution of $Ti(OEt)_4$ in methoxyethanol (i.e. 4.4 mg of $Ti(OEt)_4$ dissolved in 8.6 mg of methoxyethanol) were added to the white solid. The mixture was then subjected to the following temperature and pressure profile:
195° C. at Patm until melt of the mixture
185° C. (2 h) at Patm
185° C. (1 h) at 200 mbar
215° C. (30 min) at 80 mbar
215° C. (1 h) at 60 mbar
215° C. (1 h30) at 3 mbar
205° C. (17 h) at 3 mbar 11.6 g of a transparent oil solidifying as a white solid were recovered in vessel B2 (84 wt % of the reaction medium). $^1$H-NMR analysis of the content of B2 showed the following composition: 57% glycolide and 2.3% glycolic acid, the remainder being glycolic acid oligomers. The global yield in glycolide was 51%.

Example 2

Example 1 was reproduced except that the mixture glycolic acid/water was kept at 110° C. during 60 hours rather than 80 hours (but the same quantity of water was recovered in B2) and that 32 mg of a 35 wt % solution of $Ti(OEt)_4$ in methoxyethanol (i.e. 11.4 mg of $Ti(OEt)_4$ dissolved in 20.6 mg of methoxyethanol) were added, rather than 13 mg of a 34 wt % solution.

11.7 g of a transparent oil solidifying as a white solid were recovered in vessel B2 (85 wt % of the reaction medium). $^1$H-NMR analysis of the content of B2 showed the following composition: 58% glycolide and 2.6% glycolic acid, the remainder being glycolic acid oligomers. The global yield in glycolide was 52%.

Example 3

Example 2 was reproduced except that the mixture glycolic acid/water was kept at 110° C. during 80 hours rather than 60 hours (but the same quantity of water was recovered in B2) and that the temperature and pressure profile was modified as follows:
195° C. at Patm until melt of the mixture
185° C. (2 h) at Patm
185° C. (1 h) at 200 mbar
185° C. (1 h) at 60 mbar
185° C. (17 h) at 3 mbar 7.75 g of a transparent oil solidifying as a white solid were recovered in vessel B2 (57 wt % of the reaction medium). 1H-NMR analysis of the content of B2 showed the following composition: 61.1% glycolide and 2.4% glycolic acid, the remainder being glycolic acid oligomers. The global yield in glycolide was 37%.

Example 4 (Comparative—No Polyol)

17.0 g of pure (99%) solid glycolic acid and 7.5 g of water (to solubilize the glycolic acid) were introduced into the 80 ml BÜCHI round-bottomed flask (B1) and said flask was placed in a ventilated oven at 110° C. during about 17 hours. After 80 hours, a white solid was present in B1 and 10.9 g of water were collected in B2.

26 mg of a 34 wt % solution of $Ti(OEt)_4$ in methoxyethanol (i.e. 8.7 mg of $Ti(OEt)_4$ dissolved in 17.3 mg of methoxyethanol) were added to the white solid.

The mixture was then subjected to the following temperature and pressure profile:
215° C. (2 h) at Patm
215° C. (1 h) at 200 mbar
215° C. (30 min) at 80 mbar
215° C. (1 h) at 60 mbar
215° C. (1 h30) at 3 mbar
180° C. (17 h) at 3 mbar Only 2.3 g of product were recovered in vessel B2 (18 wt % of the reaction medium), corresponding mainly to glycolic acid.

Example 5 (Comparative—No Catalyst)

17.0 g of pure (99%) solid glycolic acid, 7.5 g of water (to solubilize the glycolic acid) and 1.4 g of ethylene glycol (22.6 mmol or 45 mmol of OH functions) were introduced into the 80 ml BÜCHI round-bottomed flask (B1) and said flask was placed in a ventilated oven at 110° C. during about 60 hours. After 60 hours, a white solid was present in B1 and 11.9 g of water were collected in B2. The mixture was then subjected to the following temperature and pressure profile:

185° C. (2 h) at Patm
215° C. (1 h) at 200 mbar
215° C. (30 min) at 80 mbar
215° C. (1 h) at 60 mbar
215° C. (3 h) at 3 mbar
180° C. (17 h) at 3 mbar Only 4.5 g of product were recovered in vessel B2 (32 wt % of the reaction medium), corresponding mainly to glycolic acid.

Example 6 (Comparative—No Catalyst)

17.0 g of pure (99%) solid glycolic acid and 7.5 g of water (to solubilize the glycolic acid) were introduced into the 80 ml BÜCHI round-bottomed flask (B1) and said flask was placed in a ventilated oven at 110° C. during about 60 hours. After 60 hours, a white solid was present in B1 and 11.0 g of water were collected in B2.

1.41 g of distilled ethylene glycol (22.6 mmol or 45 mmol of OH functions) were added to the white solid and the mixture was placed in a ventilated oven at 110° C. during 15 hours. 1.3 g of water were collected in B2.

The mixture was then subjected to the following temperature and pressure profile:
195° C. (2 h) at Patm
215° C. (1 h) at 200 mbar
215° C. (30 min) at 80 mbar
215° C. (1 h) at 60 mbar
215° C. (3 h) at 3 mbar
180° C. (17 h) at 3 mbar Only 1.8 g of product were recovered in vessel B2 (14 wt % of the reaction medium), corresponding mainly to glycolic acid.

Examples 7-8

17.0 g of pure (99%) solid glycolic acid and 7.6 g of water (to solubilize the glycolic acid) were introduced into the 80 ml BÜCHI round-bottomed flask (B1) and said flask was placed in a ventilated oven at 110° C. during about 60 hours. After 60 hours, a white solid was present in B1 and about 11 g of water were collected in B2.

1.40 g of distilled ethylene glycol (22.5 mmol or 45 mmol of OH functions) and $Ti(OEt)_4$ (amounts in the table below, added as 34 wt % solution in methoxyethanol) were added to the white solid.

The mixture was then subjected to the following temperature and pressure profile:
195° C. at Patm until melt of the mixture (about 30 min)
190° C. (1.5 h) at Patm
190° C. (1 h) at 200 mbar
215° C. (1 h) at 80 mbar
225° C. (1 h 30) at 50 mbar
240° C. (17-22 h) at a pressure below 1 mbar The duration of the distillation, the amount of catalyst, and the global yield in glycolide are summarized in the table below.

| Ex. | Duration (h) | $Ti(OEt)_4$ (mg) | mppm $Ti(OEt)_4$ | Mass in B2 (g) | wt % glycolide in B2 | Global yield in glycolide (%) |
|---|---|---|---|---|---|---|
| 7 | 22 | 5.2 | 100 | 10.4 | 81 | 65 |
| 8 | 17 | 7.1 | 138 | 13.5 | 70 | 73 |

Examples 9-11

Examples 7-8 were reproduced except the temperature and pressure profile which was as follows:
195° C. (2 h) at Patm
215° C. (1 h) at 200 mbar
225° C. (2 h) at 50 mbar
225° C. (2 h) at 10 mbar
240° C. (17-22 h) at a pressure below 1 mbar The duration of the distillation, the amount of catalyst, and the global yield in glycolide are summarized in the table below

| Example | Duration (h) | $Ti(OEt)_4$ (mg) | mppm $Ti(OEt)_4$ | Mass in B2 (g) | wt % glycolide in B2 | Global yield in glycolide (%) |
|---|---|---|---|---|---|---|
| 9 | 17 | 7.9* | 152 | 13.6 | 70 | 73 |
| 10 | 15 | 14.2* | 274 | 13.8 | 73 | 77 |
| 11 | 18 | 8.8** | 172 | 10.7 | 86 | 71 |

*$Ti(OEt)_4$ added as 34 wt % solution in methoxyethanol
**$Ti(OEt)_4$ added as a solution in the 1.40 g of ethylene glycol (no methoxyethanol)

The invention claimed is:

1. A process for the manufacture of a cyclic diester of an alpha-hydroxyacid, comprising heating an alpha-hydroxyacid at a temperature from 100 to 250° C. in the presence of at least one polyol and of at least one catalyst selected from the group consisting of carboxylates and alkoxides of Ti, Zr, Al and Sn.

2. The process according to claim 1, wherein said alpha-hydroxyacid is selected from the group consisting of lactic acid, glycolic acid, glutaric acid, mandelic acid, malic acid, citric acid, and tartaric acid.

3. The process according to claim 1, wherein said heating is conducted at a temperature from 150 to 240° C.

4. The process according to claim 1, wherein said heating is conducted under a pressure equal to or lower than 500 mbar.

5. The process according to claim 1, wherein said heating is initiated at atmospheric pressure, then continues under a progressive vacuum until a pressure of from 10 to 200 mbar is attained.

6. The process according to claim 1, wherein said polyol is selected from the group consisting of ethylene glycol, propylene glycol, diethylene glycol, glycerol, erythritol, mannitol, sorbitol, xylitol, maltitol, lactitol, and volemitol.

7. The process according to claim 1, wherein said polyol is added in an amount of from 2 to 50 mol % of the alpha-hydroxyacid.

8. The process according to claim 1, wherein said catalyst is selected from the group consisting of carboxylates and alkoxides of titanium, zirconium, aluminum and tin.

9. The process according to claim 1, wherein said catalyst is added in an amount of from 50 to 300 mppm of the alpha-hydroxyacid.

10. The process according to claim 1, wherein said heating is conducted in the absence of a solvent.

11. The process according to claim 1, wherein said heating is conducted in the presence of at least one organic solvent.

12. The process according to claim 11, wherein said solvent is present in an amount of from 10 to 50 wt % of the reaction medium.

13. The process according to claim 11, wherein said alpha-hydroxyacid is heated at a temperature from 80 to 150° C., during from 12 to 36 hours, prior to the addition of said polyol and of said catalyst.

14. The process according to claim 13, wherein said heating is conducted at atmospheric pressure.

15. The process according to claim 1, wherein said cyclic diester of said alpha-hydroxyacid is collected by distillation under reduced pressure.

16. The process according to claim 2, wherein said alpha-hydroxyacid is glycolic acid.

17. The process according to claim 6, wherein said polyol is ethylene glycol.

18. The process according to claim 7, wherein said polyol is added in an amount of from 5 to 20 mol % of said alpha-hydroxyacid.

19. A process for the manufacture of a cyclic diester of an alpha-hydroxyacid, said process comprising heating an alpha-hydroxyacid selected from the group consisting of lactic acid and glycolic acid at a temperature from 100 to 250° C. in the presence of at least one polyol selected from the group consisting of ethylene glycol, propylene glycol, diethylene glycol, glycerol, erythritol, mannitol, sorbitol, xylitol, maltitol, lactitol and volemitol, and of at least one catalyst selected from the group consisting of titanium alkoxides.

20. A process for the manufacture of a cyclic diester of glycolic acid, said process comprising heating glycolic acid at a temperature from 100 to 250° C. in the presence of ethylene glycol and of at least one catalyst selected from the group consisting of titanium tetramethoxide, titanium tetraethoxide, and titanium tetraisopropoxide, wherein ethylene glycol is added in an amount of from 5 to 20 mol % of glycolic acid.

\* \* \* \* \*